United States Patent
Tsai et al.

(10) Patent No.: US 10,507,041 B2
(45) Date of Patent: Dec. 17, 2019

(54) BIONIC FIXING APPARATUS AND APPARATUS FOR PULLING OUT THE SAME

(71) Applicants: INDUSTRIAL TECHNOLOGY RESEARCH INSTITUTE, Hsinchu (TW); NATIONAL TAIWAN UNIVERSITY HOSPITAL, Taipei (TW)

(72) Inventors: Pei-Yi Tsai, Hsinchu (TW); Chih-Chieh Huang, Zhunan Township (TW); Yi-Hung Wen, Hsinchu (TW); Hsin-Hsin Shen, Zhudong Township (TW); Yi-Hung Lin, Zhubei (TW); De-Yau Lin, Tainan (TW); Jui-Sheng Sun, Taipei (TW); Chuan-Sheng Chuang, Taichung (TW); An-Li Chen, Tainan (TW); Ching-Chih Lin, Kaohsiung (TW)

(73) Assignees: INDUSTRIAL TECHNOLOGY RESEARCH INSTITUTE, Hsinchu (TW); NATIONAL TAIWAN UNIVERSITY HOSPITAL, Taipei (TW)

(*) Notice: Subject to any disclaimer, the term of this patent is extended or adjusted under 35 U.S.C. 154(b) by 888 days.

(21) Appl. No.: 14/555,251

(22) Filed: Nov. 26, 2014

(65) Prior Publication Data
US 2015/0150557 A1    Jun. 4, 2015

Related U.S. Application Data

(60) Provisional application No. 61/908,772, filed on Nov. 26, 2013.

(30) Foreign Application Priority Data

Jun. 30, 2014    (TW) ............... 103122519 A (51) Int. Cl.
A61B 17/68    (2006.01)

(52) U.S. Cl.
CPC ................... *A61B 17/686* (2013.01)

(58) Field of Classification Search
CPC .............................. A61F 2002/0835
(Continued)

(56) References Cited

U.S. PATENT DOCUMENTS 2,232,336 A * 2/1941 Meersteiner ........... B21H 3/027
                                                    408/219
2,913,031 A * 11/1959 McKay ................... F16B 39/34
                                                    411/304
(Continued)

FOREIGN PATENT DOCUMENTS

CN    1088423 A    6/1994
CN    1098281 A    2/1995
(Continued)

OTHER PUBLICATIONS

Taiwanese Office Action and Search Report for Taiwanese Application No. 103118970, dated Feb. 15, 2016.
(Continued)

*Primary Examiner* — David W Bates
(74) *Attorney, Agent, or Firm* — Birch, Stewart, Kolasch & Birch, LLP (57) ABSTRACT

A bionic fixing apparatus is provided. The bionic fixing apparatus includes a body having a through hole and at least one slit. The through hole penetrates the body from the top surface to the bottom surface to form a top opening and a bottom opening. An inner diameter of the top opening is larger than an inner diameter of the bottom opening. The slit is connected to the bottom opening and extends upwardly from the bottom surface of the body, such that the body has a flexible bottom portion.

13 Claims, 7 Drawing Sheets

(58) Field of Classification Search
USPC .................................... 411/395, 417–418
See application file for complete search history.

(56) References Cited

U.S. PATENT DOCUMENTS

| | | | | |
|---|---|---|---|---|
| 2,956,293 | A * | 10/1960 | McKay | B23G 9/002 220/288 |
| 3,277,504 | A * | 10/1966 | Smyth | F16B 39/34 470/11 |
| 4,003,287 | A * | 1/1977 | Ziaylek, Jr. | F16B 37/127 411/418 |
| 4,636,121 | A * | 1/1987 | Miller | F16B 39/04 411/140 |
| 5,116,337 | A * | 5/1992 | Johnson | A61B 17/8625 411/178 |
| 5,370,695 | A | 12/1994 | Meuli et al. | |
| 5,876,434 | A | 3/1999 | Flomenblit et al. | |
| 7,322,983 | B2 * | 1/2008 | Harris | A61B 17/8057 606/273 |
| 8,388,660 | B1 | 3/2013 | Abdou | |
| 8,535,357 | B2 | 9/2013 | Stone et al. | |
| 8,628,582 | B2 * | 1/2014 | Lavi | A61B 17/562 606/300 |
| 9,155,578 | B2 | 10/2015 | Chegini et al. | |
| 9,308,035 | B2 * | 4/2016 | Biedermann | A61B 17/7258 |
| 2002/0198527 | A1 | 12/2002 | Muckter | |
| 2004/0122431 | A1 | 6/2004 | Biedermann et al. | |
| 2004/0162560 | A1 * | 8/2004 | Raynor | A61B 17/7032 606/278 |
| 2004/0210217 | A1 | 10/2004 | Baynham et al. | |
| 2005/0112397 | A1 | 5/2005 | Rolfe et al. | |
| 2005/0143823 | A1 | 6/2005 | Boyd et al. | |
| 2005/0192675 | A1 | 9/2005 | Robinson | |
| 2006/0100630 | A1 | 5/2006 | West, Jr. | |
| 2006/0106390 | A1 | 5/2006 | Jensen et al. | |
| 2007/0038221 | A1 * | 2/2007 | Fine | A61F 2/0811 606/323 |
| 2007/0141110 | A1 * | 6/2007 | Stone | A61B 17/866 424/423 |
| 2007/0265622 | A1 | 11/2007 | Aeschlimann et al. | |
| 2009/0240289 | A1 | 9/2009 | Zipprich et al. | |
| 2010/0042215 | A1 | 2/2010 | Stalcup et al. | |
| 2011/0123951 | A1 | 5/2011 | Lomicka | |
| 2011/0166602 | A1 | 7/2011 | Malek | |
| 2011/0213423 | A1 | 9/2011 | Biedermann et al. | |
| 2011/0307073 | A1 | 12/2011 | Teoh et al. | |
| 2012/0184993 | A1 | 7/2012 | Arambula et al. | |
| 2012/0271362 | A1 | 10/2012 | Martineau et al. | |
| 2013/0030529 | A1 | 1/2013 | Hunt | |
| 2013/0123862 | A1 * | 5/2013 | Anderson | A61B 17/88 606/321 |
| 2014/0288649 | A1 | 9/2014 | Hunt | |
| 2015/0093717 | A1 | 4/2015 | Ali | |
| 2015/0112342 | A1 * | 4/2015 | Penzimer | A61B 17/8875 606/63 |

FOREIGN PATENT DOCUMENTS

| | | |
|---|---|---|
| CN | 1204498 A | 1/1999 |
| CN | 1604759 A | 4/2005 |
| CN | 1891172 A | 1/2007 |
| CN | 2894638 Y | 5/2007 |
| CN | 101198291 A | 6/2008 |
| CN | 201082188 Y | 7/2008 |
| CN | 101317790 A | 12/2008 |
| CN | 201840550 U | 5/2011 |
| CN | 202682036 U | 1/2013 |
| CN | 202821579 U | 3/2013 |
| CN | 103167837 A | 6/2013 |
| EP | 1 112 722 A2 | 7/2001 |
| EP | 1 069 872 B1 | 5/2003 |
| EP | 1 762 189 A1 | 3/2007 |
| EP | 2400901 B1 | 5/2013 |
| TW | 330839 | 5/1998 |
| TW | 480169 B | 3/2002 |
| TW | 200416020 A | 9/2004 |
| TW | 200635565 A | 10/2006 |
| TW | 200708295 A | 3/2007 |
| TW | 200722036 A | 6/2007 |
| TW | I306396 B | 2/2009 |
| TW | 200936113 A | 9/2009 |
| TW | 200944176 A1 | 11/2009 |
| TW | 201100061 A | 1/2011 |
| TW | 201221108 A1 | 6/2012 |
| TW | 201235005 A1 | 9/2012 |
| TW | 201240653 A | 10/2012 |
| TW | 201249392 A1 | 12/2012 |
| TW | 201325577 A1 | 7/2013 |
| TW | 201325638 A1 | 7/2013 |
| TW | M458938 U | 8/2013 |
| WO | 2011/059995 A2 | 5/2011 |
| WO | WO 2012/024665 A2 | 2/2012 |
| WO | WO 2013/043218 A1 | 3/2013 |
| WO | WO 2013/043432 A1 | 3/2013 |

OTHER PUBLICATIONS

Taiwanese Office Action and Search Report for Taiwanese Application No. 103122519, dated Dec. 2, 2015.
Taiwanese Office Action and Search Report for Taiwanese Application No. 103122817, dated Nov. 26, 2015.
Chinese Office Action and Search Report dated Jan. 17, 2017 for Application No. 201410406040.6.
Taiwanese Office Action and Search Report dated Feb. 18, 2017 for Application No. 104140981.
"Setting the Stage for What is Next", 2012 United States Medical Devices Outlook, NB3E-54, Jul. 2012.
Achour et al., "Stress distribution in dental implant with elastomeric stress barrier", Materials and Design, 2011, vol. 32, pp. 282-290.
Breguet et al., "Compact, Light Weight Mechanisms for High Precision Micro-Manipulators", pp. 1-5.
Chen et al., "Pullout strength for cannulated pedicle screws with bone cement augmentation in severely osteoporotic bone: Influences of radial hole and pilot hole tapping", Clinical Biomechanics, 2009, vol. 24, pp. 613-618.
Emmelmann et al, "Laser freeform fabrication of porous network structures for dental application", Proceedings of the Fifth International WLT-Conference on Lasers in Manufacturing 2009, Munich, Jun. 2009, pp. 453-457.
Kissel et al., "Comparison of Pullout Strength of Small-Diameter Cannulated and Solid-Core Screws", The Journal of Foot & Ankle Surgery, Nov./Dec. 2003, vol. 42, No. 6, pp. 334-338.
Lin et al., "A biomechanical study of the cortex-anchorage vertebral screw", Clinical Biomechanics, 2003, vol. 18, pp. S25-S32.
Liu et al., "Design and biomechanical study of a modified pedicle screw", Chinese Journal of Traumatology, 2010, vol. 13, No. 4, pp. 222-228.
Migliorati et al., "Miniscrew design and bone characteristics: An experimental study of primary stability"; AJO-DO, Aug. 2012, vol. 142, No. 2, pp. 228-234.
Mikos et al., "Laminated three-dimensional biodegradable foams for use in tissue engineering", Biomaterials, 1993, vol. 14, No. 5, pp. 323-330.
Richman, MD, "Odontoid Screw Fixation for Type II Odontoid Fractures", Operative Techniques in Orthopaedics, Jan. 1998, vol. 8, No. 1, pp. 16-21.
Shen et al., "Hollow-Bone-Graft Dynamic Hip Screw Can Fix and Promote Bone Union after Femoral Neck Fracture: an Experimental Research", International Journal of Medical Sciences, 2012, vol. 9, No. 10, pp. 916-922: doi:10.7150/ijms.4567.
Sumner et al., "Functional adaptation and ingrowth of bone vary as a function of hip implant stiffness", Journal of Biomechanics, 1998, vol. 31, pp. 909-917.
U.S. Office Action, dated Sep. 7, 2017, for U.S. Appl. No. 14/554,521.
U.S. Office Action, dated Dec. 26, 2017, for U.S. Appl. No. 14/977,234.

(56) References Cited

OTHER PUBLICATIONS

U.S. Office Action for U.S. Appl. No. 14/554,521, dated Sep. 17, 2018.

* cited by examiner

BIONIC FIXING APPARATUS AND APPARATUS FOR PULLING OUT THE SAME

CROSS-REFERENCE TO RELATED APPLICATION

This application claims the benefits of U.S. provisional application 61/908,772, filed Nov. 26, 2013, and Taiwan application Serial No. 103122519, filed Jun. 30, 2014, the disclosures of which are incorporated by reference herein in its entirety.

TECHNICAL FIELD

The technical field relates to a bionic fixing apparatus and an apparatus for pulling out the same.

BACKGROUND

With the advances in technology and medicine, implants, such as bone screws, are used to fix the biological tissue in the human body for medical purpose, for example, for repairing accidental injury or nature aging. However, after a conventional implant is fixed in the human body, it easily detaches from the human body along the path which is used for implanting the conventional implant when the fixing position is receiving force. Besides, when a soft tissue is near the fixing position, the soft tissue is usually fixed by using biodegradable materials. However, the effect of the biodegradable materials on human body is concerned in medical community. For example, the biodegradable materials may remain in the human body and not be successfully discharged, or the biodegradable materials may cause biological cell disease.

Further, after implanting the implant to the human body, if the implant generates adverse reactions and need to be removed, there may be no suitable means which can easily take out the implant from the human body, which often causes damage to biological tissues.

SUMMARY

The disclosure is directed to a bionic fixing apparatus having a flexible bottom portion. A specific structure is formed on the surface of the implants or insides the implants by additive manufacturing process, which may effectively decrease modulus of elasticity of the implants and prevent the implants from detaching from the human body along the path which is used for implanting the implants. Further, the disclosure is also directed to an apparatus for pulling out the bionic fixing apparatus, which may easily take out the implants from the human body.

According to one embodiment, a bionic fixing apparatus is provided. The bionic fixing apparatus includes a body having a through hole and at least one slit. The through hole penetrates the body from the top surface to the bottom surface to form a top opening and a bottom opening. An inner diameter of the top opening is larger than an inner diameter of the bottom opening. The slit is connected to the bottom opening and extends upwardly from the bottom surface of the body, such that the body has a flexible bottom portion.

According to another embodiment, an apparatus for pulling out a bionic fixing apparatus from an organism is provided. The bionic fixing apparatus includes a body having a through hole, an inner screw thread and an outer screw thread disposed in the inner surface and the outer surface of the body respectively. The apparatus for pulling out the bionic fixing apparatus includes a control portion and a rotating portion connected to the control portion. The rotating portion is screwed into the through hole towards a screw-in direction, such that the bionic fixing apparatus is screwed out from the organism towards a direction opposite to the screw-in direction of the rotating portion.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The embodiments are described in details with reference to the accompanying drawings. The identical elements of the embodiments are designated with the same reference numerals. Also, it is important to point out that the illustrations may not be necessarily drawn to scale, and that there may be other embodiments of the present disclosure which are not specifically illustrated. Thus, the specification and the drawings are regarded as an illustrative sense rather than a restrictive sense.

Figure 1A:
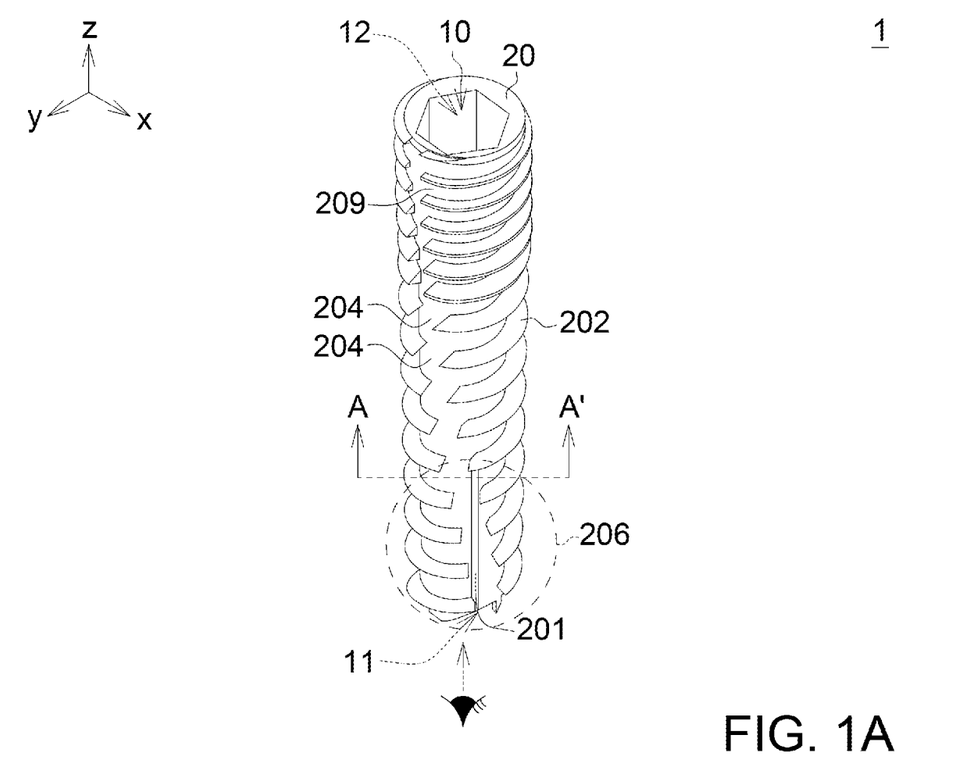
FIG. 1A illustrates a bionic fixing apparatus according to the embodiment of the disclosure.
Figure 1B:
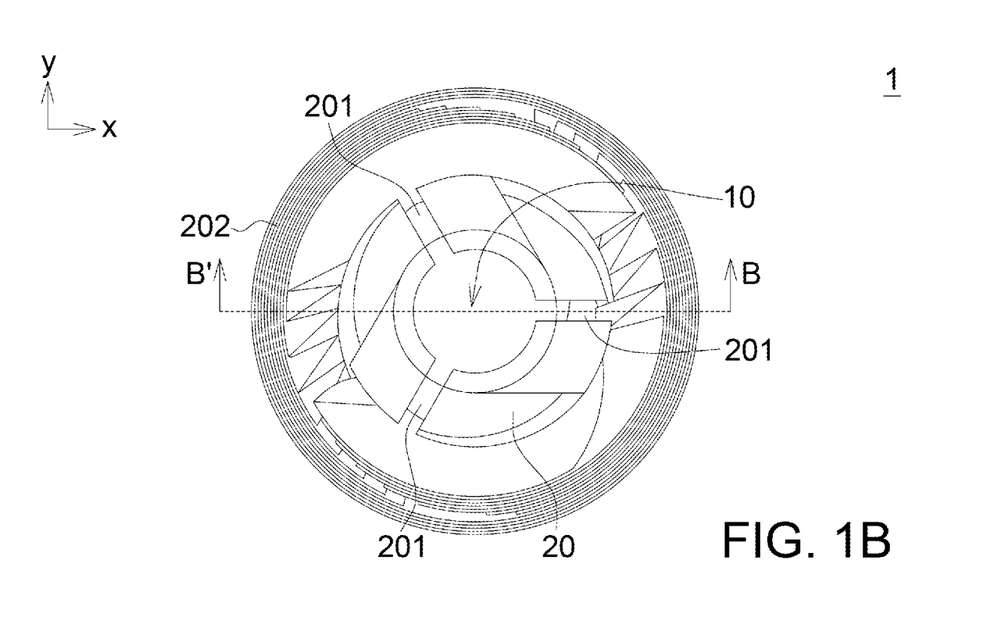
FIG. 1B illustrates a cross-sectional view of the bionic fixing apparatus along A-A' line in FIG. 1A, which is viewed from the bottom portion towards the top portion of the bionic fixing apparatus.

FIG. 1A illustrates a bionic fixing apparatus 1 according to the embodiment of the disclosure. FIG. 1B illustrates a cross-sectional view of the bionic fixing apparatus 1 along A-A' line in FIG. 1A, which is viewed from the bottom portion towards the top portion of the bionic fixing apparatus 1.

As shown in FIGS. 1A and 1B, the bionic fixing apparatus 1 according to the embodiment of the disclosure includes a body 20 having a through hole 10 and at least one slit 201. The through hole 10 penetrates the body 20 from the top surface to the bottom surface to form a top opening 12 and a bottom opening 11. An inner diameter of the top opening 12 is larger than an inner diameter of the bottom opening 11. The slit 201 is connected to the bottom opening 11 and extended upwardly from the bottom surface of the body 20, such that the body 20 has a flexible bottom portion 206. That is, the slit 201 is extended from the outer surface 209 of the body 20 to the through hole 10 and penetrates the flexible bottom portion 206. In this embodiment, the body 20 may include an outer screw thread 202 disposed on the outer surface 209 of the body 20.

In one embodiment, the body 20 may have a plurality of slits 201. For example, the body 20 has three slits 201 as shown in FIG. 1B, but the disclosure is not limited thereto.

Figure 2A:
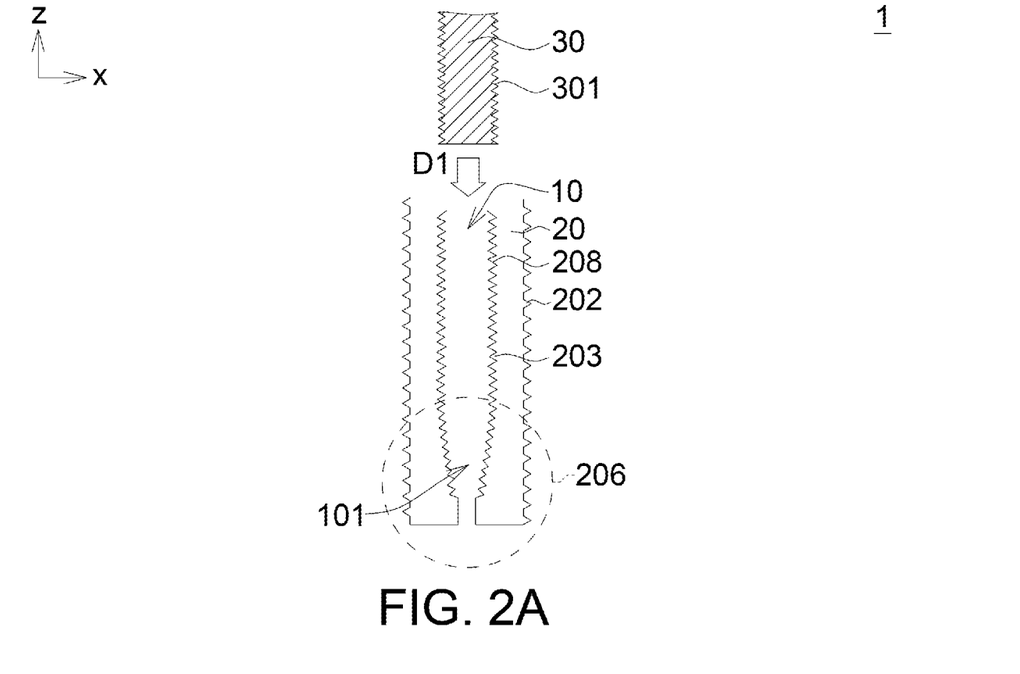
FIG. 2A illustrates a simplified cross-sectional view of the bionic fixing apparatus along B-B' line in FIG. 1A on the X-Z plane.

FIG. 2A illustrates a simplified cross-sectional view of the bionic fixing apparatus 1 along B-B' line in FIG. 1B on the X-Z plane. It should be noted that, in order to facilitate showing the technical features of the embodiment of the disclosure, the following figures show simplified schematic diagrams, and some elements and the connecting relationship between the elements may be omitted. As shown in FIG. 2A, the bottom portion 101 of the through hole 10 of the bionic fixing apparatus 1 according to the embodiment of the disclosure is such as conical. Here, the bottom portion 101 corresponds to the position of the flexible bottom portion 206 of the body 20. Besides, the bionic fixing apparatus 1 may further include an inner fixing structure 30 disposed in the flexible bottom portion 206, and the inner fixing structure 30 may be fixed in the flexible bottom portion 206.

Figure 2B:
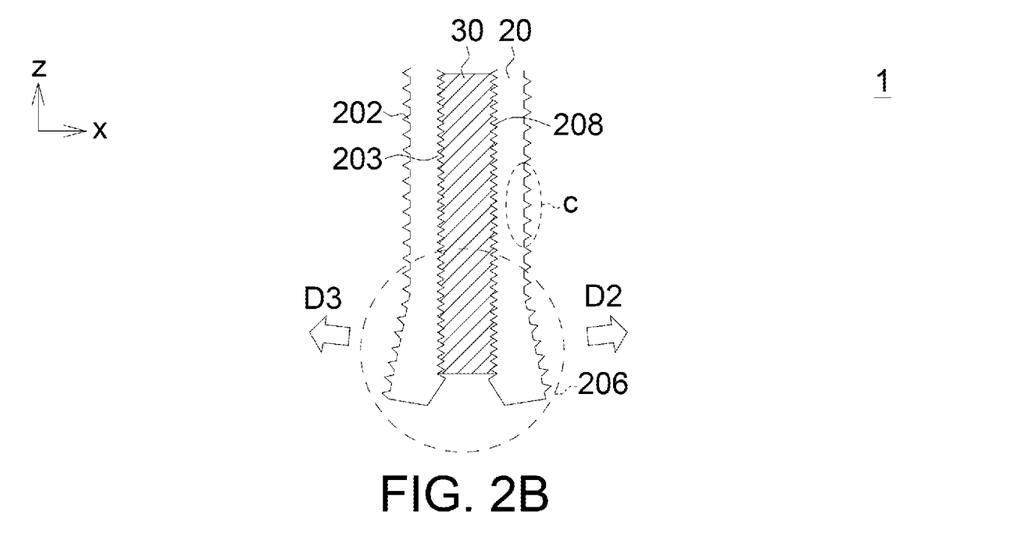
FIG. 2B illustrate a simplified schematic diagram of the inner fixing structure fixing in the through hole.

FIG. 2B illustrate a simplified schematic diagram of the inner fixing structure 30 fixing in the through hole 10. In this embodiment, the body 20 may include an inner screw thread 203 disposed on the inner surface 208 of the body 20. A thread direction of the inner screw thread 203 and a thread direction of the outer screw thread 202 may be the same or opposite.

As shown in FIG. 2A and FIG. 2B, the inner fixing structure 30 may be a screw with screw thread 301 disposed on the surface. The inner fixing structure 30 may be rotated into the through hole 10 along a first direction D1 by the screw thread 301 and the inner screw thread 203 of the body 20. In this embodiment, the first direction D1 is such as parallel to a direction (or an implanted direction) along which the bionic fixing apparatus 1 is implanted to an organism. That is, the bottom portion may be implanted to the organism first to implant the bionic fixing apparatus 1.

As shown in FIG. 2B, when the inner fixing structure 30 is rotated to reach the flexible bottom portion 206, the flexible bottom portion 206 is pushed and generates deformation because of the design of the slit 201 and the conical bottom portion 101 of the through hole 10. The flexible bottom portion 206 is deformed and pushed outwardly along the directions D2 and D3 by the inner fixing structure 30 as shown in FIG. 2B.

In the embodiment of the disclosure, the bionic fixing apparatus 1 is fixed in an organism by the outer screw thread 202 of the body 20. That is, when the flexible bottom portion 206 is deformed and pushed outwardly by the inner fixing structure 30, the flexible bottom portion 206 is expanded outwardly and fixed in the organism tighter. Even the bionic fixing apparatus receives an outer force along a direction (a pulling-out direction) opposite to the first direction D1, the outer screw thread 202 of the bionic fixing apparatus 1 fixed in the organism won't be easily taken out from the organism.

It should be noted that although the inner fixing structure 30 is a screw in the embodiment above of the disclosure, and the inner fixing structure 30 is fixed in the through hole 10 by the inner screw thread 203 of the body 20, but the disclosure is not limited thereto. Instead, other non-screw structures, for example, tenons or other similar structures may be used for fixing the inner fixing structure 30 to the flexible bottom portion 206, such that the bionic fixing apparatus 1 may be pushed outwardly by the inner fixing structure 30, and fixed in the organism tighter.

When the inner fixing structure 30 is fixed in the through hole 10, the bionic fixing apparatus 1 is flexible because of the flexible bottom portion 206 and the slit 201. Therefore, the flexible bottom portion 206 of the body may not be destroyed by the inner fixing structure 30, and only be pushed outwardly and deformed, such that the bionic fixing apparatus 1 may be fixed in the organism tighter.

Figure 3A:
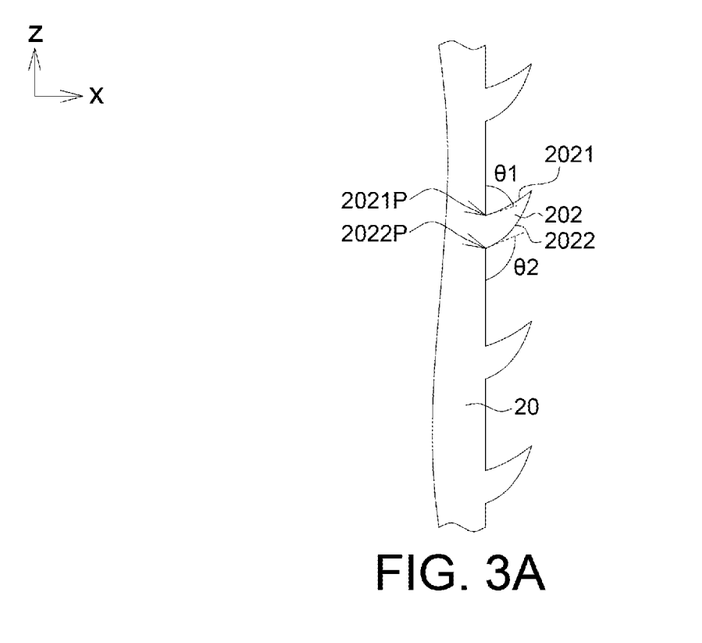
FIG. 3A illustrates a partial enlarged view of area C in FIG. 2B.

Further, the outer screw thread 202 may have different embodiments in the disclosure. FIG. 3A illustrates a partial enlarged view of area C in FIG. 2B. As shown in FIG. 3A, the outer screw thread 202 has a first inclined side 2021 and a second inclined side 2022 on a longitudinal section (a cross-section along B-B' line on the X-Z plane, parallel to a direction along which the bionic fixing apparatus 1 is implanted to an organism) of the body 20. An included angle between the first inclined side 2021 and the body 20 is a first exterior angle θ1, and an included angle between the second inclined side 2022 and the body 20 is a second exterior angle θ2. In this embodiment, the first inclined side 2021 is nearer to the top opening 12 than the second inclined side 2022.

In this embodiment, the first exterior angle θ1 is smaller than 90 degrees, and the second exterior angle θ2 is larger than 90 degrees. That is, the outer screw thread 202 according to the embodiment of the disclosure presents a barb shape cross-section on X-Z plane, such that even the bionic fixing apparatus 1 receives an outer force along the direction (the pulling-out direction) opposite to the first direction D1, the bionic fixing apparatus 1 won't be easily taken out from the organism.

It should be noted that the first inclined side 2021 and the second inclined side 2022 of the outer screw thread 202 may be arc lines. As shown in FIG. 3A, when the first inclined side 2021 and the second inclined side 2022 are arc lines, the first exterior angle θ1 is defined as an included angle between the body 20 and the tangent line of the contact point 2021P (at which the first inclined side 2021 contacts the body 20); the second exterior angle θ2 is defined as an included angle between the body 20 and the tangent line of the contact point 2022P (at which the second inclined side 2022 contacts the body 20).

Figure 3B:
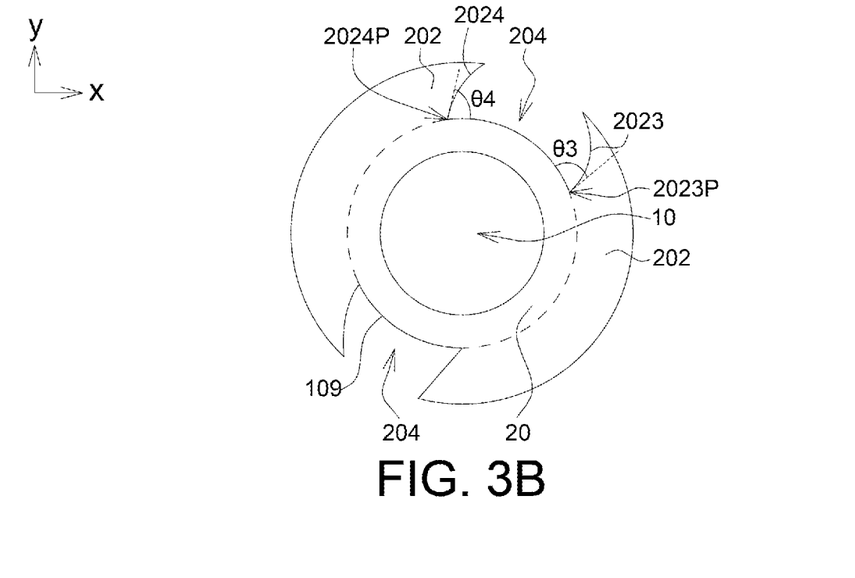
FIG. 3B illustrates a cross-section view of the outer screw thread in the transverse section of the body (X-Y plane).

FIG. 3B illustrates a cross-section view of the outer screw thread 202 in the transverse section of the body 20 (X-Y plane). In this embodiment, the transverse section of the body 20 is perpendicular to the first direction D1 and the longitudinal section (X-Z plane). As shown in FIG. 3B, the outer screw thread 202 has a third inclined side 2023, a fourth inclined side 2024, and at least one interval area 204 on the transverse section of the body 20. The third inclined side 2023 and the fourth inclined side 2024 are on the opposite sides of the interval area 204 respectively. Besides, an included angle between the third inclined side 2023 and the body 20 is a third exterior angle θ3, and an included angle between the fourth inclined side 2024 and the body 20 is a fourth exterior angle θ4. The third exterior angle θ3 and the fourth exterior angle θ4 are larger than 0 and smaller than 90 degrees.

Similarly, the third inclined side 2023 and the fourth inclined side 2024 of the outer screw thread 202 may be arc lines. As shown in FIG. 3B, when the third inclined side 2023 and the fourth inclined side 2024 are arc lines, the third exterior angle θ3 is defined as an included angle between the body 20 and the tangent line of the contact point 2023P (at which the third inclined side 2023 contacts the body 20); the fourth exterior angle θ4 is defined as an included angle between the body 20 and the tangent line of the contact point 2024P (at which the fourth inclined side 2024 contacts the body 20).

The outer screw thread 202 according to the embodiment of the disclosure may have a plurality of interval areas 204 on the transverse section of the body 20. As shown in FIG. 3B, the outer screw thread 202 has two interval areas 204 in this embodiment. Referring to FIG. 1A, the outer screw thread 202 is discontinuous because of the plurality of interval areas 204.

When the bionic fixing apparatus 1 is implanted into an organism, bone chips may be generated. For example, the bionic fixing apparatus 1 is used as a bone screw and screwed into a human body by the outer screw thread 202, and the bone chips may be collected in the plurality of interval areas 204, such that the goal of collecting bone chips may be achieved. Further, the third inclined side 2023 and the fourth inclined side 2024 may make the outer screw thread 202 to be a barb shape, such that after the bionic fixing apparatus 1 is implanted into an organism, it is not easy to take out the bionic fixing apparatus 1 along a path opposite to the path of screwing the bionic fixing apparatus 1 into the organism, because the bone chips collected in the interval areas 204 hinder the barb-shaped outer screw thread 202 to prevent the bionic fixing apparatus 1 from being taken out.

Figure 4A:
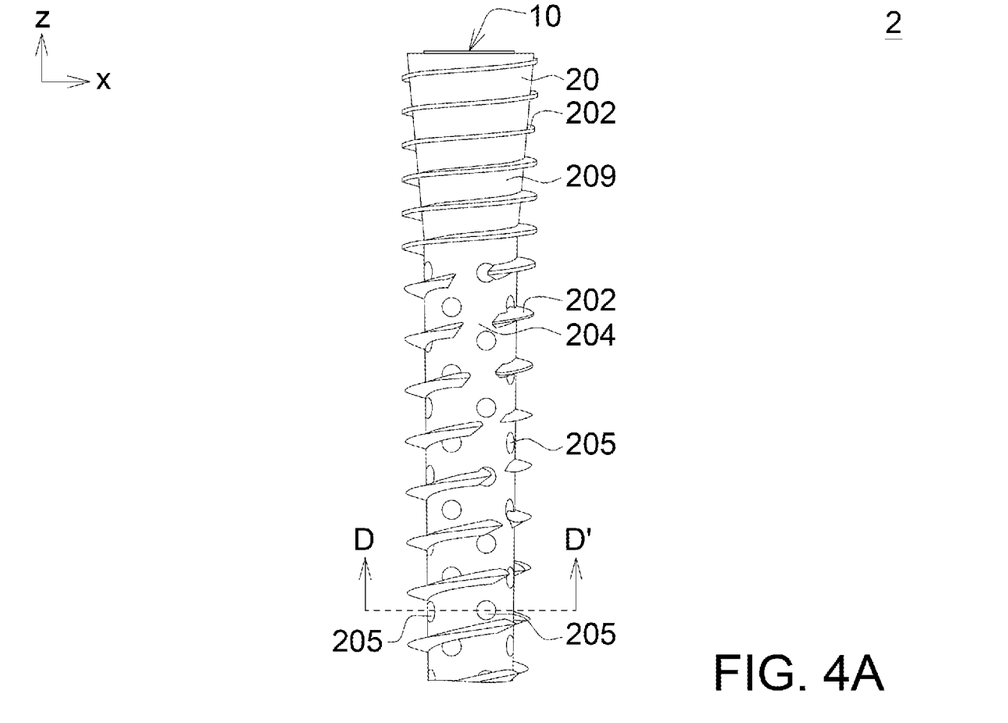
FIG. 4A illustrates the bionic fixing apparatus according to another embodiment of the disclosure.

FIG. 4A illustrates the bionic fixing apparatus 2 according to another embodiment of the disclosure. Similar to the bionic fixing apparatus 1 in FIG. 1, the bionic fixing apparatus 2 also includes a body 20 having a through hole 10. Besides, the body 20 may include an outer screw thread 202 disposed on the outer surface 209 of the body 20.

Figure 4B:
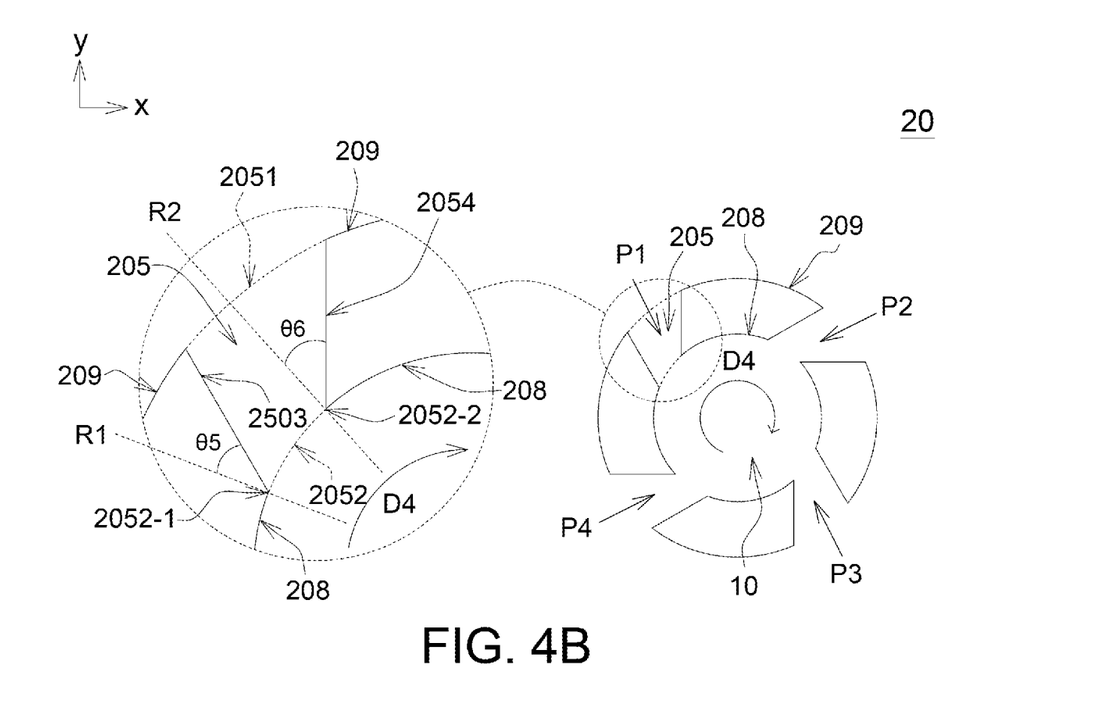
FIG. 4B illustrates a cross-sectional view of the bionic fixing apparatus along D-D' line in FIG. 4A.

In this embodiment, the body 20 may include a plurality of pores 205. FIG. 4B illustrates a cross-sectional view of the bionic fixing apparatus 2 along D-D' line in FIG. 4A. It should be noted that FIG. 4B is a simplified schematic diagram, and some elements (such as outer screw thread 202 and inner screw thread 203) are omitted, such that the structure of the pores 205 may be shown more clearly.

As shown in FIG. 4B, the pores 205 are extended from the outer surface 209 of the body 20 to the through hole 10. When the bionic fixing apparatus 2 is screwed into an organism, hard tissues of the organism, such as bone chips, are collected and enter the through hole 10 along a path from the pores 205 to the through hole 10. For example, the bionic fixing apparatus 2 used as a bone screw is screwed along a rotating direction D4 into the bone of a human body. At this moment, bone chips may be generated by the outer screw thread 202 and enter the through hole 10 along paths P1, P2, P3 and P4, such that the bone chips may be collected in the through hole 10 of the bionic fixing apparatus 2.

In the embodiment of the disclosure, the size of the pores and the path extending to the through hole 10 may be adjusted according to the rotating direction of the bionic fixing apparatus 2. For example, the pores 205 may form a first opening 2051 on the outer surface 209 of the body 20 and a second opening 2052 on the inner surface 208 of the body 20. The second opening 2052 has a first end 2052-1 and a second end 2052-2 on the inner surface 208 of the body 20. In this embodiment, an area of the first opening 2051 is larger than an area of the second opening 2052.

Further, the body 20 has a first side wall 2053 and a second side wall 2054 disposed on both sides of each of the pores 205 respectively, and the second side wall 2054 faces the first side wall 2053. The first side wall 2053 is formed by rotating a first reference plane R1 with a first angle θ5 along the rotating direction D4 (or a tangential direction of the outer surface 209 of the body 20). Here, the first reference plane R1 is perpendicular to the outer surface 209 and inner surface 208 of the body 20, and passes through the first end 2052-1 of the second opening 2052. The second side wall 2054 is formed by rotating a second reference plane R2 with a second angle θ6 along the rotating direction D4 (or a tangential direction of the outer surface 209 of the body 20). Here, the second reference plane R2 is perpendicular to the outer surface 209 and inner surface 208 of the body 20, and passes through the second end 2052-2 of the second opening 2052.

In this embodiment, the first angle θ5 and the second angle θ6 are larger than 0 and smaller than 90 degrees, and the first angle θ5 is smaller than the second angle θ6. Such structure may make the area of the first opening 2051 larger than the area of the second opening 2052, which promotes the hard tissue (such as bone chips) being collected in the through hole 10 by the pores 205.

Besides, the outer screw thread 202 of the bionic fixing apparatus 2 may also have at least one interval area 204 for collecting such as bone chips. When the bionic fixing apparatus 2 is implanted into an organism, hard tissues (such as bone chips) may be collected in the interval area 204 of the outer screw thread 202, or penetrate through the body 20 by the pore 205 and be collected in the through hole 10 rapidly. Conversely, when the space of the through hole 10 is occupied by the hard tissues of the organism, the excess hard tissues may be quickly discharged through the body 20 by the pores 205 and the interval area 204 of the outer screw thread 202 (chips removal).

In one embodiment, the bionic fixing apparatus 2 may also include a body having at least one slit 201 (not show in FIG. 4A). The slit 201 may be disposed on the bottom portion of the body 20 and extended from the outer surface 209 to the through hole 10.

Figure 5A:
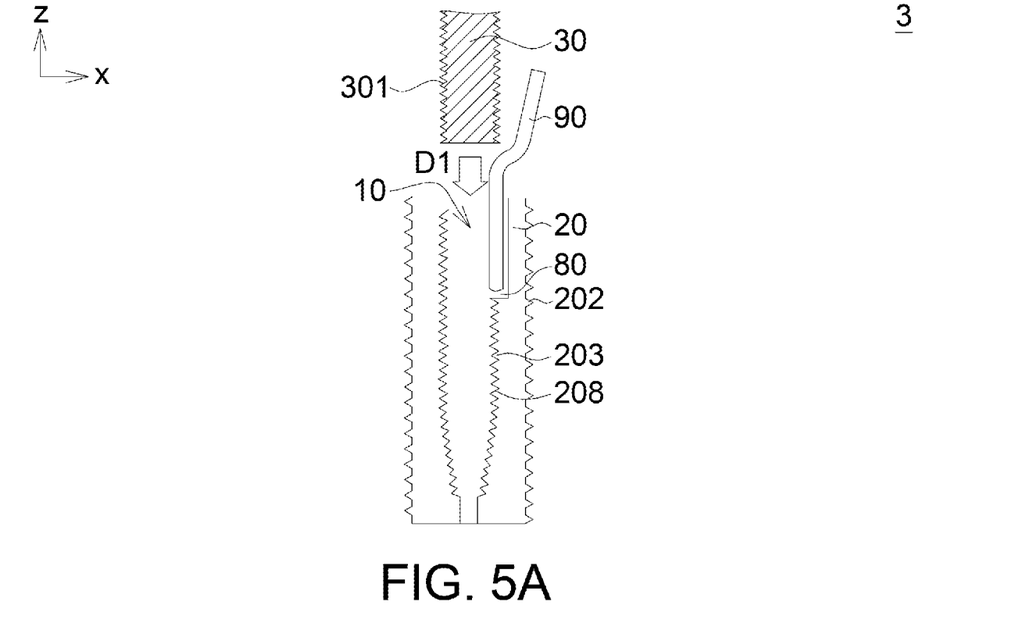
FIGS. 5A and 5B illustrate the bionic fixing apparatus for fixing the soft tissue according to the embodiment of the disclosure.
Figure 5B:
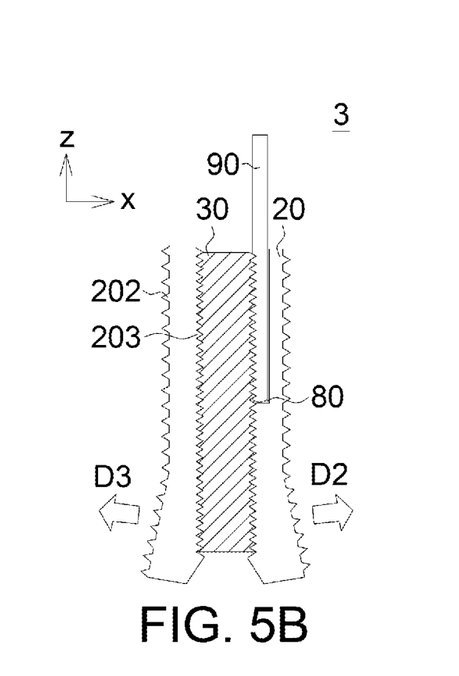
Figure 5C:
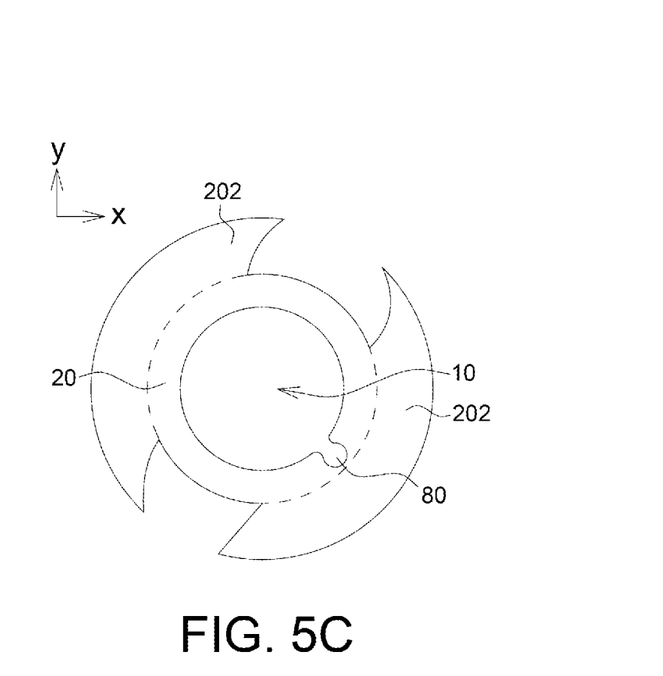
FIG. 5C illustrates a cross-section view of the bionic fixing apparatus in the transverse section (X-Y plane).

In some embodiments, the bionic fixing apparatus according to the disclosure may be applied to fix the soft tissue 90 of an organism (referring to FIG. 5A-5C). FIGS. 5A and 5B illustrate the bionic fixing apparatus 3 for fixing the soft tissue 90 according to the embodiment of the disclosure. FIG. 5C illustrates a cross-section view of the bionic fixing apparatus 3 in the transverse section (X-Y plane). The structure of the bionic fixing apparatus 3 is similar to the structure of the bionic fixing apparatus 1 as shown in FIGS. 2A and 2B, and similar elements would not be narrated in detail herein.

As shown in FIG. 5A-5C, the body 20 of the bionic fixing apparatus 3 may include a capacitive space 80. The capacitive space 80 may be disposed adjacent to the inner surface 208 of the body 20, such that soft tissues 90 of an organism may be contained in the capacitive space 80 and fixed in the bionic fixing apparatus 3. In this embodiment, the soft tissues 90 of the organism may be such as ligaments. Because of the capacitive space 80, the soft tissues may be fixed in the bionic fixing apparatus 3 while the inner fixing structure 30 is fixed in the through hole 10.

For example, the soft tissues 90 may be placed in the capacitive space 80 first, and then be fixed in the capacitive space 80 of the body 20 until the inner fixing structure 30 is screwed and fixed into the through hole 10.

Similarly, other non-screw structures (such as tenons) may be used for fixing the soft tissues 90 into the body 20 of the bionic fixing apparatus 3 while fixing the inner fixing structure 30 to the through hole 10. Besides, it is also possible to use additional ways, such as using sutures to enhance fixing the soft tissues 90.

In conventional ways to fix the soft tissues 90, biodegradable bone screws are used. However, the biodegradable screws may generate the reaction to foreign body, and cause the tissues abrasion. Besides, the effect of the biodegradable materials on human body after degradation is still doubted in medical community. Instead, fixing the soft tissues 90 by the bionic fixing apparatus 3 according to the embodiment of the disclosure may effectively solve the problems by the conventional ways mentioned above.

As mentioned in the embodiments above, since the bionic fixing apparatus includes the through hole 10 and the body 20, the bionic fixing apparatus may be fixed in the hard tissues (such as bones) of the organism by the outer screw thread 202 of the body 20. Further, the soft tissues 90 may be fixed in the capacitive space 80 of the body 20 by the through hole 10, the capacitive space 80 and the inner fixing structure 30. Therefore, the bionic fixing apparatus may be fixed in the organism tighter to prevent the bionic fixing apparatus from being taken out from the organism effectively.

In one embodiment, the thread direction of the inner screw thread 203 of the body 20 and the thread direction of the outer screw thread 202 of the body 20 are the same. In another embodiment, the thread direction of the inner screw thread 203 of the body 20 and the thread direction of the outer screw thread 202 of the body 20 are opposite.

In addition, the complex micro-structure in the embodiments mentioned above may be manufactured by an additive manufacturing (AM) process. The outer screw thread 202 and inner screw thread 203 of the body 20, or the slit 201 and the pores 205 in the embodiments are all one-piece formed. Further, various shapes and arrangements according to the embodiments of the disclosure may be easily completed by the additive manufacturing process. On the contrary, the conventional process (including a special sintering process or a surface coating process to the implants, and then executing a surface treatment by laser to enhance bone integration) is not only more complex, but also needs more manufacturing cost, which is not suitable to manufacture the structures in the embodiments of the disclosure.

In the embodiments of the disclosure, a material of the bionic fixing apparatus may include metals, alloys, ceramics or polymeric biomaterials. In addition, the through hole 10 and the slit 201 or the pores 205 may produce an atmosphere which is more suitable for cells or tissues of organisms growing therein.

Further, the bionic fixing apparatus according to the embodiments of the disclosure may be applied to fix different parts of the organism. For example, the bionic fixing apparatus may be applied to an artificial tooth root, vertebral screws, artificial discs, intramedullary nails or bone screws. Since the bionic fixing apparatus may be manufactured by the additive manufacturing process, it is easy to design different structures to correspond to different parts of the organism.

Figure 6A:
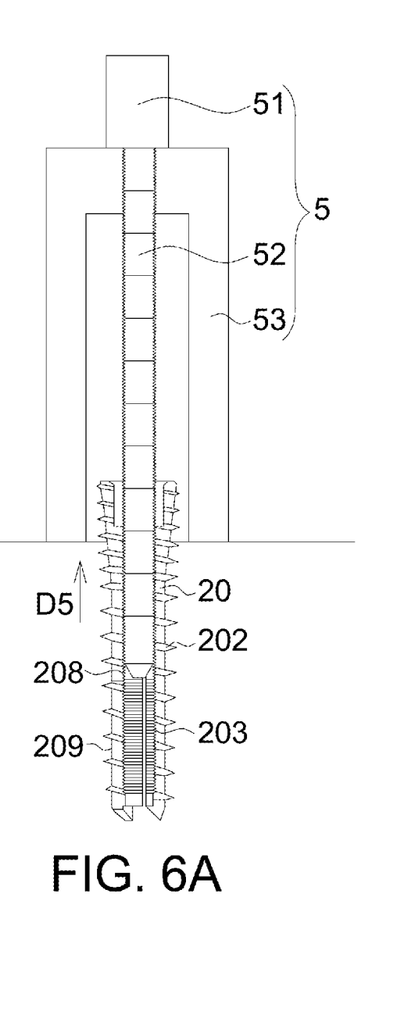
FIGS. 6A and 6B illustrate the apparatus for pulling out a bionic fixing apparatus from an organism according to the embodiment of the disclosure.
Figure 6B:
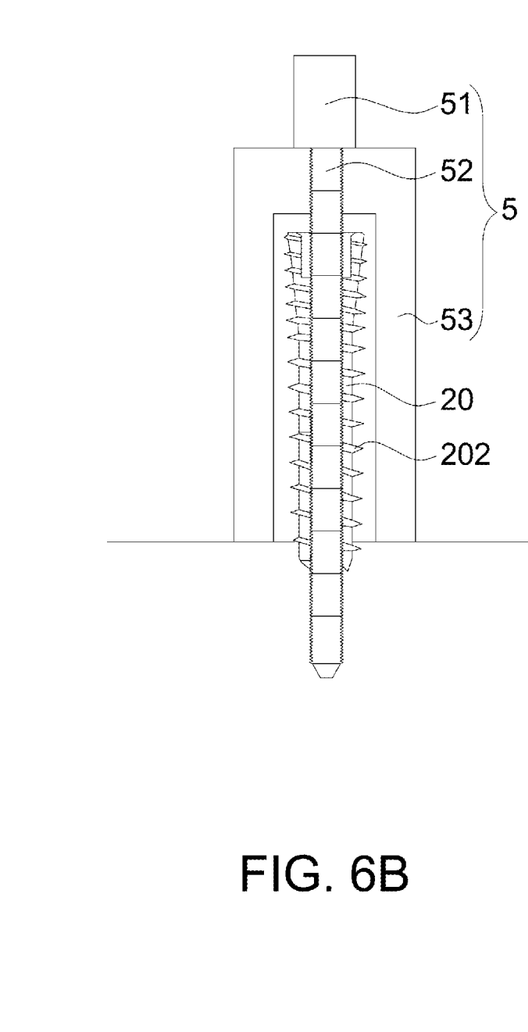

FIGS. 6A and 6B illustrate the apparatus 5 for pulling out a bionic fixing apparatus from an organism according to the embodiment of the disclosure. In this embodiment, the bionic fixing apparatus is such as the bionic fixing apparatus 1 shown in FIG. 1A. The bionic fixing apparatus 1 includes a body 20. The body 20 may have a through hole 10, an inner screw thread 203 and an outer screw thread 202 disposed in the inner surface 208 and the outer surface 209 of the body 20 respectively. Besides, a thread direction of the inner screw thread 203 and a thread direction of the outer screw thread 202 are opposite.

The apparatus 5 for pulling out the bionic fixing apparatus according to the embodiment of the disclosure includes a control portion 51 and a rotating portion 52. The rotating portion 52 is connected to the control portion 51, and the rotating portion 52 is screwed into the through hole 10 by the inner screw thread 203 of the body 20, such that the bionic fixing apparatus 1 may be screwed out from the organism.

In this embodiment, the apparatus 5 for pulling out the bionic fixing apparatus may further include a fixing portion 53. The fixing portion 53 may prevent the control portion 51 and the rotating portion 52 from moving along a direction (D5) of pulling out the bionic fixing apparatus 1. For example, when the rotating portion 52 is screwed into the through hole 10 by the inner screw thread 203 of the body of the bionic fixing apparatus 1, the fixing portion 53 may fix the position of the control portion 51 and the rotating portion 52, such that the control portion 51 and the rotating portion 52 would not move along the direction D5 (which is a direction for pulling out the bionic fixing apparatus 1). Instead, the bionic fixing apparatus 1 may move along the direction D5 while the rotating portion is screwed in the through hole towards a screw-in direction. In this embodiment, the direction D5 is parallel to a direction for pulling out the bionic fixing apparatus 1. The bionic fixing apparatus 1 may be screwed out from the organism since the bionic fixing apparatus 1 may move along the direction D5.

Figure 7A:
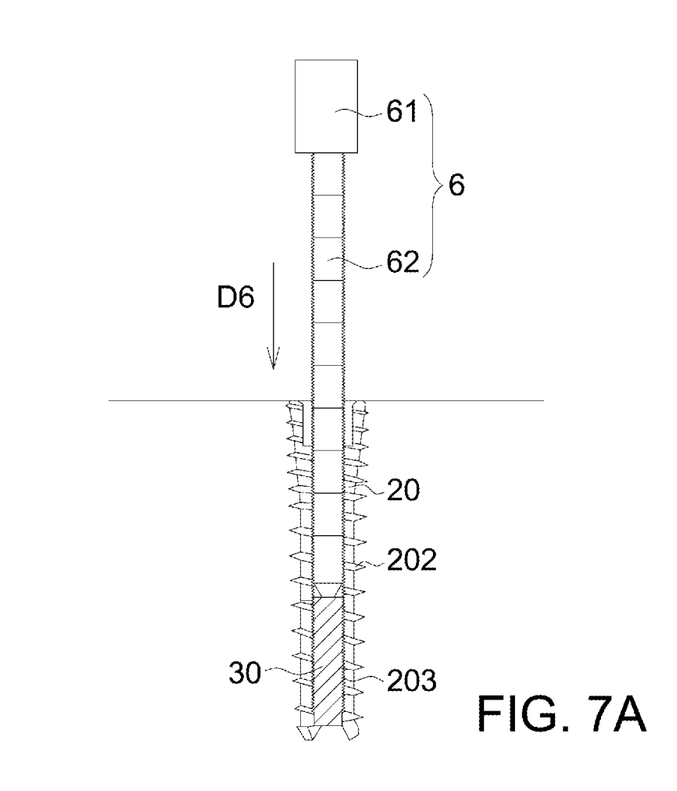
FIGS. 7A and 7B illustrate the apparatus for pulling out a bionic fixing apparatus from an organism according to another embodiment of the disclosure.
Figure 7B:
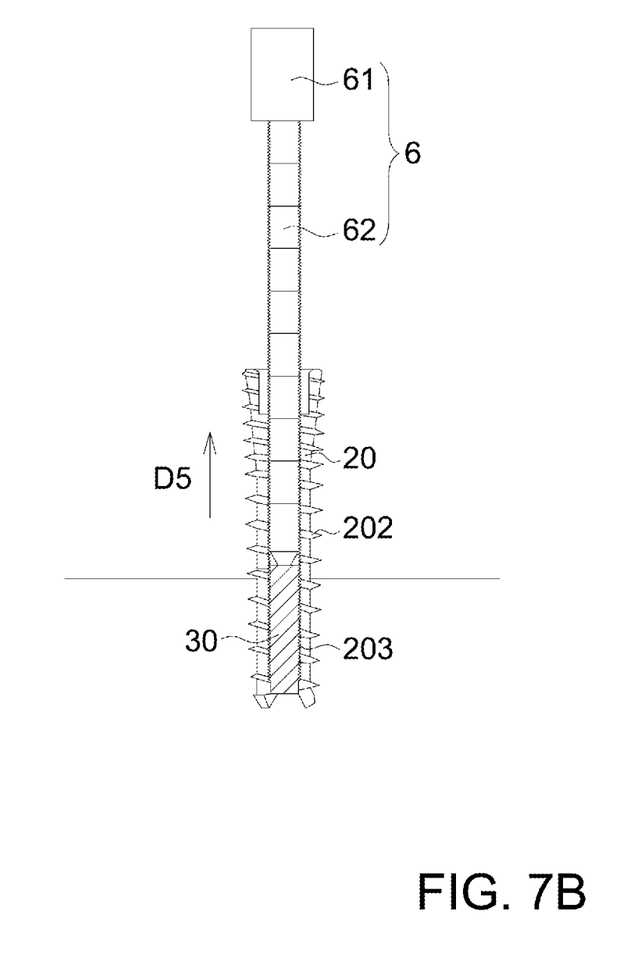

FIGS. 7A and 7B illustrate the apparatus 6 for pulling out a bionic fixing apparatus from an organism according to another embodiment of the disclosure. In this embodiment, the bionic fixing apparatus is such as the bionic fixing apparatus 1 shown in FIG. 1. Besides, the bionic fixing apparatus 1 may include an inner fixing structure 30 disposed in the bottom portion of the through hole 10.

The apparatus 6 for pulling out the bionic fixing apparatus according to the embodiment of the disclosure includes a control portion 61 and a rotating portion 62, and the rotating portion 62 is screwed into the through hole 10 by the inner screw thread 203 of the body 20, such that the bionic fixing apparatus 1 may be screwed out from the organism.

It is different from the apparatus 5 for pulling out the bionic fixing apparatus shown in FIGS. 5A and 5B that the apparatus 6 for pulling out the bionic fixing apparatus may not have a fixing portion 53. Since a thread direction of the inner screw thread 203 and a thread direction of the outer screw thread 202 are opposite, when the rotating portion 62 of the apparatus 6 is screwed into the through hole 10 along a screw-in direction, the bionic fixing apparatus 1 is screwed out towards a direction opposite to the screw-in direction.

For example, the rotating portion 62 is screwed into the bottom portion of the through hole 10 by the inner screw thread 203 of the body 20, or the rotating portion 62 is screwed into the through hole 10 until contacting the inner fixing structure 30 as shown in FIG. 7A, such that the rotating portion 62 may not move along a direction D6 with respect to the bionic fixing apparatus 1. Here, the direction D6 is parallel to a direction for implanting the bionic fixing apparatus 1 into the organism.

Then, the rotating portion is rotated continuously, and the rotating portion may bring the whole bionic fixing apparatus 1 to rotate. Here, since the thread direction of the inner screw thread 203 and the thread direction of the outer screw thread 202 are opposite, the bionic fixing apparatus 1 may be rotated along a direction opposite to the direction for screwing the bionic fixing apparatus 1 into the organism, and may move towards the direction D5 as shown in FIG. 7B. In this embodiment, the direction D5 is parallel to a direction for pulling out the bionic fixing apparatus 1. The bionic fixing apparatus 1 may be screwed out from the organism since the bionic fixing apparatus 1 may move along the direction D5.

Therefore, if the adverse reactions happen and needs to be removed after the bionic fixing apparatus is implanted into the organism, then it may easily take out the bionic fixing apparatus from the organism by the embodiments mentioned above, and it may not damage the biological tissues.

Compared with the fixing structure with high modulus of elasticity such as conventional bone screw, the bionic fixing apparatus according to the embodiments of the disclosure having the specific structure on the surface or the inner portion by the additive manufacturing process may effectively decrease modulus of elasticity of the implants to prevent from stress concentration and stress shielding. Furthermore, the bionic fixing apparatus according to the embodiments of the disclosure may prevent the tissue of organisms from sagging, necrosis, wearing, or to prevent the implants from being broken or damaged.

In addition, the bionic fixing apparatus may not detach from the human body along the path which is used for implanting the bionic fixing apparatus because of the specific screw thread structures (such as the structures shown in FIGS. 3A and 3B). Further, if the adverse reactions happen and needs to be removed after the bionic fixing apparatus is implanted into the organism, then it may easily take out the bionic fixing apparatus from the organism.

Furthermore, various shapes and arrangements of the pores according to the embodiments of the disclosure may be easily completed by the additive manufacturing process. On the contrary, the conventional process (including a special sintering process or a surface coating process to the implants, and then executing a surface treatment by laser to enhance bone integration) is not only more complex, but also needs more manufacturing cost, which is not suitable to manufacture the structures in the embodiments of the disclosure.

The additive manufacturing process may also be known as rapid prototyping (RP), rapid manufacturing (RM) or 3D Printing. It is rectified as additive manufacturing process by American Society for Testing and Materials (ASTM) in 2009. Researchers have divided the additive manufacturing process into seven types as show in Table 1. The seven types include: Vat Photopolymerization, Material Jetting, Binder Jetting, Material Extrusion, Powder Bed Fusion, Sheet Lamination, and Directed Energy Deposition.

TABLE 1

| Process | Material | Application |
| --- | --- | --- |
| Vat Photopolymerization | photopolymers | Prototyping |
| Material Jetting | polymers, waxes | Prototyping |
| Binder Jetting | polymers, metals | Casting Pattern |
| Material Extrusion | foundry sand | Prototyping, Casting Molds, Direct Part |
| Powder Bed Fusion | polymers | Prototyping |
| Sheet Lamination | polymers, metals | Prototyping, Direct Part |

TABLE 1-continued

| Process | Material | Application |
| --- | --- | --- |
| Directed Energy Deposition | paper, metals | Prototyping, Direct Part |

The characteristics of the additive manufacturing process are that the three-dimensional (3D) image is transferred to two-dimensional (2D) cross-sections, and products can be made layer by layer according to the two-dimensional cross-sections, to form a three-dimensional object. Compared with the conventional process, the additive manufacturing process may avoid wasting materials, and be more suitable for application of highly complicated structure, customized, and small or medium amount of production.

During the manufacturing process of the bionic fixing apparatus according to the embodiments of the disclosure, the 3D digital model of the bionic fixing apparatus is transferred to a 2D cross-section having thickness between 20-50 μm. And a feeding system will spread out a 20-50 μm thickness layer of powder materials (such as metals, alloys, ceramics or polymeric biomaterials) with particle size smaller than 25 μm in a low-oxygen atmosphere (concentration of $O_2$ is smaller than 10,000 ppm).

Then, the fiber laser beam (with wavelength 1070 nm) is focused to the laminated area (50-150 μm) by the scanning galvanometer. The focused beam is moved corresponding to the 2D cross-sections (the moving speed is 500-1500 mm/s), such that the powder materials is heating up above their melting point to adding a layer of structure. By repeating this procedure, the 3D bionic fixing apparatus can be made layer by layer according to the 2D cross-sections. The additive manufacturing process may produce the highly complicated shapes, inner flow channels, and inner structures which are difficult to make by the conventional process.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A bionic fixing apparatus, comprising:
   a body having a through hole and at least one slit and an outer screw thread;
   wherein the through hole penetrates the body from a top surface to a bottom surface to form a top opening and a bottom opening, and a bottom portion of the through hole is conical, such that the body has a flexible bottom portion,
   wherein the outer screw thread is disposed on an outer surface of the body, the outer screw thread is discontinuous to divide into a first part and a second part, and the outer screw thread comprises at least one interval area on a transverse section of the body and between the first part and the second part,
   wherein the first part has a first inclined side on the transverse section of the body, the second part has a second inclined side on the transverse section of the body, the first and second inclined sides are on opposite sides of the interval area respectively, an included angle between the first inclined side and the body is a first exterior angle, an included angle between the second inclined side and the body is a second exterior angle, and the first exterior angle and the second exterior angle are larger than 0 and smaller than 90 degrees.

2. The bionic fixing apparatus according to claim 1, further comprising an inner fixing structure disposed in the flexible bottom portion.

3. The bionic fixing apparatus according to claim 2, wherein when the inner fixing structure is fixed in the flexible bottom portion, the flexible bottom portion is deformed and pushed outwardly.

4. The bionic fixing apparatus according to claim 1, wherein the body comprises a capacitive space configured to contain soft tissues of an organism and fix the soft tissues in the bionic fixing apparatus.

5. The bionic fixing apparatus according to claim 1, further comprising an inner screw thread disposed on an inner surface of the body.

6. The bionic fixing apparatus according to claim 5, wherein a thread direction of the inner screw thread and a thread direction of the outer screw thread are the same.

7. The bionic fixing apparatus according to claim 5, wherein a thread direction of the inner screw thread and a thread direction of the outer screw thread are opposite.

8. A bionic fixing apparatus, comprising:
a body having a through hole and at least one slit and an outer screw thread,
wherein the through hole penetrates the body from a top surface to a bottom surface to form a top opening and a bottom opening, an inner diameter of the top opening is larger than an inner diameter of the bottom opening, and the slit is connected to the bottom opening and extends upwardly from the bottom surface of the body, such that the body has a flexible bottom portion,
wherein the body further comprises a plurality of pores extended from the outer surface of the body to the through hole, the pores form a first opening on the outer surface of the body and a second opening on the inner surface of the body, and an area of the first opening is larger than an area of the second opening, and
wherein the body has a first side wall and a second side wall disposed on both sides of each of the pores respectively, the second side wall faces the first side wall, the first side wall is formed by rotating a first reference plane with a first angle along a tangential direction of the outer surface of the body, the second side wall is formed by rotating a second reference plane with a second angle along the tangential direction of the outer surface of the body, and the first reference plane and the second reference plane are perpendicular to the outer surface of the body.

9. The bionic fixing apparatus according to claim 8, wherein when the bionic fixing apparatus is screwed into an organism, hard tissues of the organism are collected and enter the through hole along a path from the pores to the through hole.

10. The bionic fixing apparatus according to claim 8, wherein the first angle and the second angle are larger than 0 and smaller than 90 degrees, and the first angle is smaller than the second angle.

11. The bionic fixing apparatus according to claim 1, wherein a material of the bionic fixing apparatus comprises metals, alloys, ceramics or polymeric biomaterials.

12. The bionic fixing apparatus according to claim 1, wherein an inner diameter of the top opening is larger than an inner diameter of the bottom opening, and the slit is connected to the bottom opening and extends upwardly from the bottom surface of the body.

13. The bionic fixing apparatus according to claim 1, wherein the outer screw thread has a third inclined side and a fourth inclined side on a longitudinal section of the body, an included angle between the third inclined side and the body is a third exterior angle, an included angle between the fourth inclined side and the body is a fourth exterior angle, the third exterior angle is smaller than 90 degrees, the fourth exterior angle is larger than 90 degrees, and the third inclined side is nearer to the top opening than the fourth inclined side.

* * * * *